US00PP17089P3

(12) United States Plant Patent
Michalik

(10) Patent No.: US PP17,089 P3
(45) Date of Patent: Sep. 12, 2006

(54) **VARIETY OF *PELARGONIUM* PLANT NAMED 'PACAPRI'**

(50) Latin Name: *Pelargonium peltatum*
Varietal Denomination: Pacapri

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 182 days.

(21) Appl. No.: 11/045,851

(22) Filed: Jan. 28, 2005

(65) Prior Publication Data

US 2006/0174388 P1 Aug. 3, 2006

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent Bell
(74) *Attorney, Agent, or Firm*—The Webb Law Firm

(57) ABSTRACT

A new and distinct flowering *Pelargonium* plant with abundant apricot colored flowers.

1 Drawing Sheet

Botanical classification: *Pelargonium peltatum.*
Varietal denomination: 'Pacapri'.

BACKGROUND OF THE INVENTION

The present invention comprises a new and distinct cultivar of *Pelargonium peltatum* known by the varietal name 'Pacapri'. The new variety was discovered in a selected breeding program in Dresden, Germany. The new variety is the result of a cross between two unnamed and unpatented selections from a collection of proprietary breeding plants. The purpose of the breeding program was to find a new variety with double flowering and an appealing color. The double flowering and growth characteristics of the new variety are similar to its parents but with different flower color. The leaf texture and numerous flowers are similar to 'Pennea' (U.S. Plant patent application Ser. No. 09/733,016). The new variety differs from 'Pennea' in flower color and growth habit. The new variety was first asexually reproduced in 2002 by cuttings and in-vitro culture in Dresden, Germany. The new variety has been trial and field tested in Dresden and has been found to retain its distinctive characteristics and remain true to type through successive propagations. Characteristics distinguishable from other varieties include:

Unique apricot flower color

Suitable for hanging baskets

DESCRIPTION OF THE DRAWING

The accompanying photographic drawing illustrates the new variety, with the color being as nearly true as is possible with color illustrations of this type.

DESCRIPTION OF THE PLANT

Figure 1:
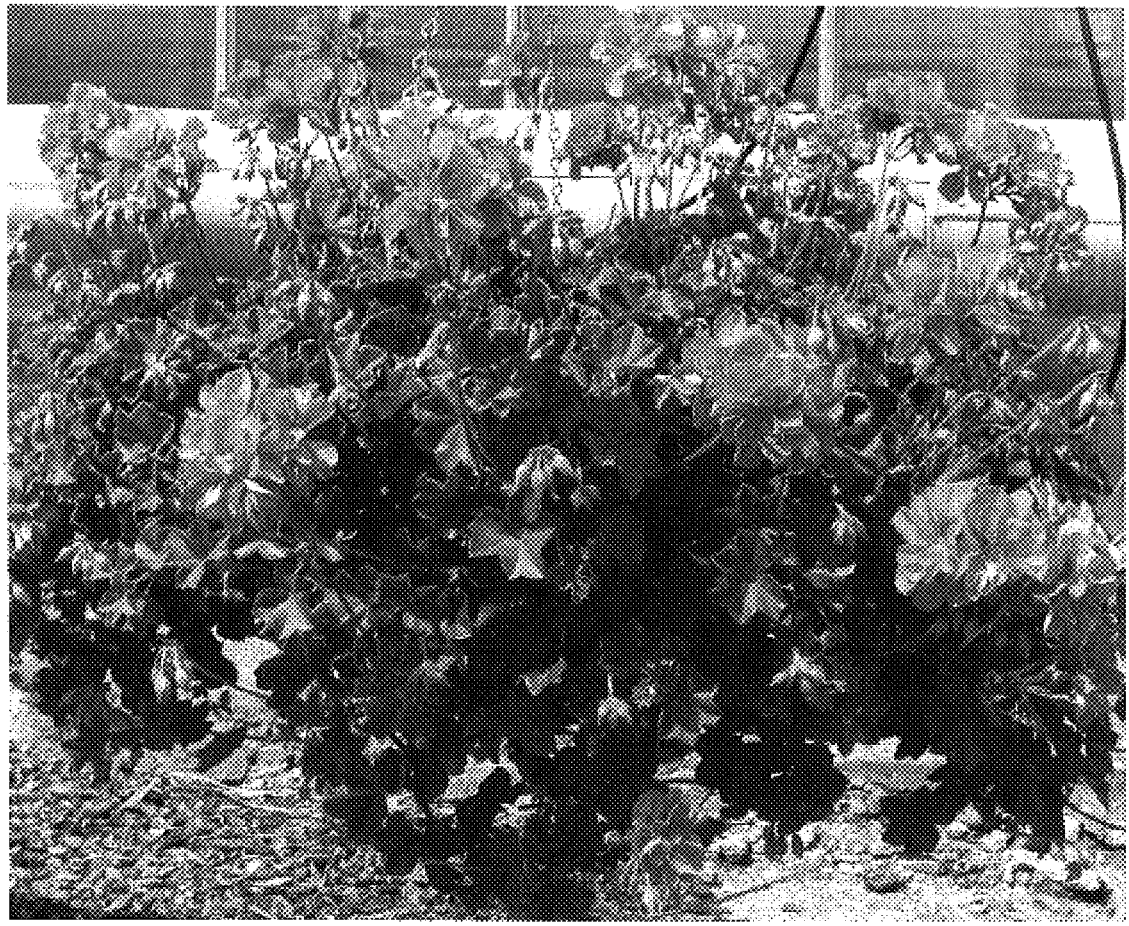

The following detailed description sets forth the characteristics of the new cultivar. The data that defines these characteristics were collected by asexual reproductions carried out in a warm greenhouse in Dresden, Germany. The color readings were taken on a plant indoors under natural light. The new variety was five months old when described. Color references are primarily to The R.H.S. Colour Chart of The Royal Horticultural Society of London.

PLANT

Form: Cascading; hanging.
Height: 12–15 cm from soil to top of foliage; 17–22 cm from soil to top of umbels.
Diameter: Approximately 25–32 cm.
Growth: Well-branched and vigorous.
Strength: Does not require artificial support; self-standing.
Time to initiate roots: About 10 days at 23° C.
Time to develop roots: About 30 days at 23° C.
Time to produce a finished flowering plant from a rooted cutting: About 11 weeks in a 12 cm container.

FOLIAGE

Arrangement: Alternate and opposite.
Leaves:
- *Size*.—Length: Approximately 3.5 cm. Width: Approximately 6.0 cm.
- *Shape*.—Overall: Typical ivy *pelargonium* leaf. Base: Open. Apex: Pointed.
- *Margin*.—Crenate.
- *Zonation*.—None present.
- *Texture*.—A bit leathery and hairy with light pubescence.
- *Aspect*.—Ivy shaped.
- *Color*.—Young Leaves: Upper surface: 144A. Lower surface: 144A. Mature Leaves: Upper surface: 146A. Lower surface: 146B.
- *Ribs and veins*.—Venation: Net-like. Color: Upper surface: About 146A, same as lamina. Lower surface: A bit lighter than 146B.

Stipules:
- *Size*.—Medium.
- *Color*.—Green, 146A (both surfaces).

Petioles:
*Color*.—Green, 146A.
*Length*.—Approximately 2.5–3.0 cm.
*Diameter*.—Approximately 1.0–2.0 mm.
Main stem:
*Length*.—10–12 cm.
*Diameter*.—3.0–5.0 mm.
*Color*.—Green, 146B.
*Internode length*.—2.0–4.5 cm.
*Texture*.—Hard.
*Pubescence*.—Medium.
Lateral branches:
*Internode length*.—2.0–4.0 cm.
*Texture*.—Hard, generally. A few branches are hairy.
*Pubescence*.—Light.
*Color*.—Green, 146B.

THE BUD (Measurements taken just prior to opening)

Shape:
*Cluster*.—Umbel.
*Individual bud*.—Elliptic.
Size:
*Cluster*.—Approximately 6.0 cm in diameter.
*Individual bud*.—Length: 1.5 cm. Width: 8.0 mm.

INFLORESCENCE

Natural flowering season: Spring and Summer until frost.
Blooming habit: Continuous.
Lastingness of an individual flower: 8–10 days.
Size:
*Diameter*.—Approximately 8.0×10 cm.
*Depth*.—Approximately 4.0–5.0 cm.
Borne: Umbel; flowers on pedicel; pedicel on peduncle.
Number of flowers per umbel: Approximately 6.
Flowers:
*Position*.—Above foliage.
*Form*.—Cupped.
*Size*.—Diameter: Approximately 5.0 cm. Depth: Approximately 1.5 cm.
*Petals*.—Number per flower: 5. Color: Upper surface: 52A. Lower surface: 52B. Tonality from a distance: Apricot. Shape: Overall: Teardrop. Apex: Round. Base: Open. Size: Length: 2.5 cm. Width: 1.8 cm. Margin: Entire; Rounded. Texture: Smooth.
Petaloids:
*Number*.—7–9.
*Shape*.—Like petals, but smaller.
*Color*.—Upper surface: 52A. Lower surface: 52B.
*Length*.—Approximately 2.2 cm.
*Width*.—Approximately 1.6 cm.
Pedicel:
*Length*.—Approximately 2.5–3.0 cm.
*Diameter*.—Approximately 2.0 mm.
*Color*.—Green 146C.
Peduncle:
*Length*.—8.0–12.0 cm.
*Diameter*.—Approximately 3.0 mm.
*Color*.—143A.
*Texture*.—Hairy.
Disease/pest resistance: No susceptibility to diseases or pests has been noted to date.
Temperature tolerance: Between 10° C.–30° C.
Fragrance: None.
Drought tolerance: None.

REPRODUCTIVE ORGANS

Stamens:
*Number per flower*.—Approximately 8.
*Anthers*.—Shape: Elliptic. Length: Approximately 1.5 to 2.0 mm. Color: Pink.
*Filament*.—Length: 6.0–9.0 mm. Color: White, generally. Sometimes there are touches of pink.
*Pollen*.—Color: Orange. Number: Uncountable.
Pistils:
*Number*.—One.
*Length*.—1.2–1.3 cm.
*Stigma*.—Shape: Spider-like. Color: Pink. Size: Medium.
*Style*.—Length: Approximately 3.0 mm. Color: White.
*Ovaries*.—Length: 2.0 mm. Width: 2.5 mm. Color: Green. Pubescence: Present.

I claim:

1. A new and distinct variety of *Pelargonium* plant substantially as shown and described.

* * * * *